US012485249B1

(12) United States Patent
Shuter et al.

(10) Patent No.: US 12,485,249 B1
(45) Date of Patent: Dec. 2, 2025

(54) RELAXATION SYSTEM WITH SCENT RELEASE

(71) Applicant: Calm and Sense Technologies, LLC

(72) Inventors: Daniel Shuter, New York, NY (US); Angela Sun, New York, NY (US); David Shuter, Palm Beach Gardens, FL (US)

(73) Assignee: CALM AND SENSE TECHNOLOGIES, LLC, Palm Beach Gardens, FL (US)

( * ) Notice: Subject to any disclaimer, the term of this patent is extended or adjusted under 35 U.S.C. 154(b) by 0 days.

(21) Appl. No.: 18/895,816

(22) Filed: Sep. 25, 2024

(51) Int. Cl.

| | |
|---|---|
| ***A61M 21/02*** | (2006.01) |
| ***A61M 11/00*** | (2006.01) |
| ***A61M 21/00*** | (2006.01) |

(52) U.S. Cl.

CPC .......... *A61M 21/02* (2013.01); *A61M 11/005* (2013.01); *A61M 2021/0016* (2013.01); *A61M 2021/0022* (2013.01); *A61M 2205/121* (2013.01); *A61M 2205/3303* (2013.01); *A61M 2205/3327* (2013.01); *A61M 2205/50* (2013.01); *A61M 2205/8206* (2013.01); *A61M 2230/005* (2013.01)

(58) Field of Classification Search

CPC ............ A61H 23/0218; A61H 23/0254; A61H 23/0263; A61H 23/0245; A61H 2201/165; A61M 21/02; A61M 11/005; A61M 11/08; A61M 2021/0016; A61M 2021/0022; A61M 2205/3303; A61B 5/486; A61B 5/0051; A61B 5/024; A61B 5/02405; A61L 9/12; A61L 9/122; A61L 9/125; A61L 9/127; A61L 9/02; A61L 9/03; A61L 9/032; A61L 9/035; A61L 9/037; A61L 9/14; B05B 17/0684; B05B 17/0646; B05B 17/0638; B05B 17/0623; B05B 17/063; B05B 17/0615; B05B 17/0607; B05B 17/06

See application file for complete search history.

(56) References Cited

U.S. PATENT DOCUMENTS

| | | | | |
|---|---|---|---|---|
| 6,129,771 A * | 10/2000 | Ficke | A61L 9/03 431/126 |
| 10,980,951 B1 * | 4/2021 | Walters | A61M 15/08 |
| 11,197,974 B2 | 12/2021 | Kremer et al. | |
| 11,260,198 B2 | 3/2022 | Rabin et al. | |
| 2010/0024812 A1 * | 2/2010 | Sugita | A61M 11/041 128/203.12 |
| 2012/0285446 A1 * | 11/2012 | Van Der Mark | B05B 17/06 128/200.14 |

(Continued)

*Primary Examiner* — Joseph D. Boecker
*Assistant Examiner* — Brian T Khong
(74) *Attorney, Agent, or Firm* — Rankin, Hill & Clark LLP

(57) ABSTRACT

A relaxation device includes an enclosure, a vibrator, a scent release mechanism, at least one processing device, and a power source. The vibrator is provided in the enclosure and is configured to induce vibrations of at least a portion of the enclosure. The scent release mechanism is at least partially mounted within the enclosure. The processing device is in electrical communication with the vibrator and the scent release mechanism and is configured to control operation of the vibrator and the scent release mechanism. The power source is in the enclosure and electrically connected with the processing device, the vibrator and the scent release mechanism.

20 Claims, 5 Drawing Sheets

(56) References Cited

U.S. PATENT DOCUMENTS

| | | | | |
|---|---|---|---|---|
| 2016/0213866 | A1* | 7/2016 | Tan | A61M 15/0021 |
| 2017/0274405 | A1* | 9/2017 | Lucas | B05B 17/0661 |
| 2018/0028441 | A1* | 2/2018 | Cashman | A61M 15/0065 |
| 2018/0373272 | A1* | 12/2018 | Kihm | A61L 9/03 |
| 2020/0245931 | A1* | 8/2020 | Chmelik | A61B 5/486 |
| 2023/0166071 | A1 | 6/2023 | Adriaenssen et al. | |
| 2024/0001069 | A1 | 1/2024 | Jun | |
| 2024/0001070 | A1 | 1/2024 | Jun | |

* cited by examiner

RELAXATION SYSTEM WITH SCENT RELEASE

BACKGROUND

Various relaxation devices have been developed to help individuals manage stress and promote relaxation. However, many existing solutions are limited in their approach, often focusing on a single sensory experience. There is a need for a more comprehensive relaxation device that can engage multiple senses simultaneously, providing a more effective and personalized relaxation experience

SUMMARY

In view of the foregoing, a relaxation device includes an enclosure, a vibrator, a scent release mechanism, at least one processing device, and a power source. The vibrator is provided in the enclosure and is configured to induce vibrations of at least a portion of the enclosure. The scent release mechanism is at least partially mounted within the enclosure. The processing device is in electrical communication with the vibrator and the scent release mechanism, and is configured to control operation of the vibrator and the scent release mechanism. The power source is in the enclosure and electrically connected with the processing device, the vibrator and the scent release mechanism.

A scent capsule for use with a relaxation device is also disclosed. The scent capsule includes a capsule housing, scent solution in the capsule housing and a capillary wick extending from an interior of the capsule housing. The capsule housing has a volume between 0.5 and 3.0 mL. The capillary wick extends through a wick opening in the capsule housing to an exterior of the capsule housing.

A method of operating a relaxation device is also disclosed. The method includes controlling a vibrator disposed in an enclosure to induce vibrations of at least a portion of the enclosure, detecting a person's cardiac signals via electrodes mounted to the enclosure and at least one processing device in electrical communication with the electrodes, and comparing the detected cardiac signals to a target cardiac signal via the at least one processing device. If the detected cardiac signals correspond to the target cardiac signal, then a scent solution is emitted from the enclosure via a scent release mechanism in electrical communication with the processing device. If the detected cardiac signals do not correspond to the target cardiac signal, then the method returns to detecting the person's cardiac signals via the electrodes mounted to the enclosure and the processing device in electrical communication with the electrodes.

DETAILED DESCRIPTION

Figure 1:
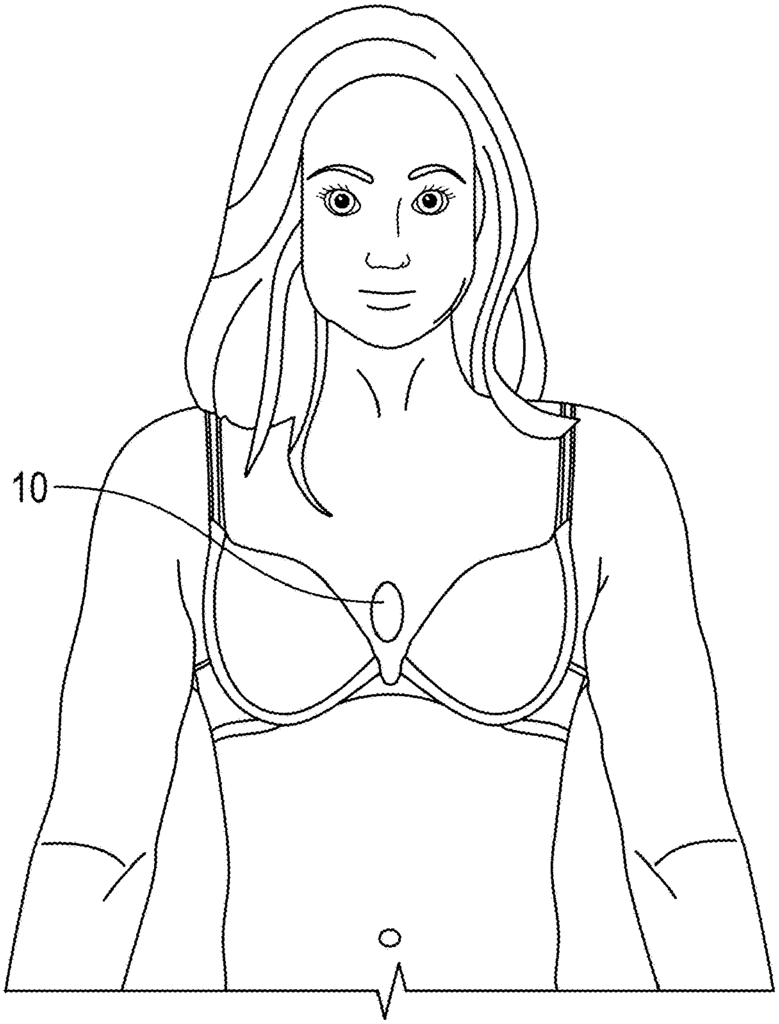
FIG. 1 is a schematic depiction of an enclosure of the relaxation device resting on a user's sternum.

The detailed description and specific examples, while describing particular embodiments, are intended for purposes of illustration only and are not intended to limit the scope of the invention. These embodiments and other features, aspects, and advantages will become better understood from the following description, appended claims, and accompanying drawings. The figures are merely schematic and may not be drawn to scale, and the same reference numerals are used throughout the figures to indicate the same or similar parts.

Figure 3:
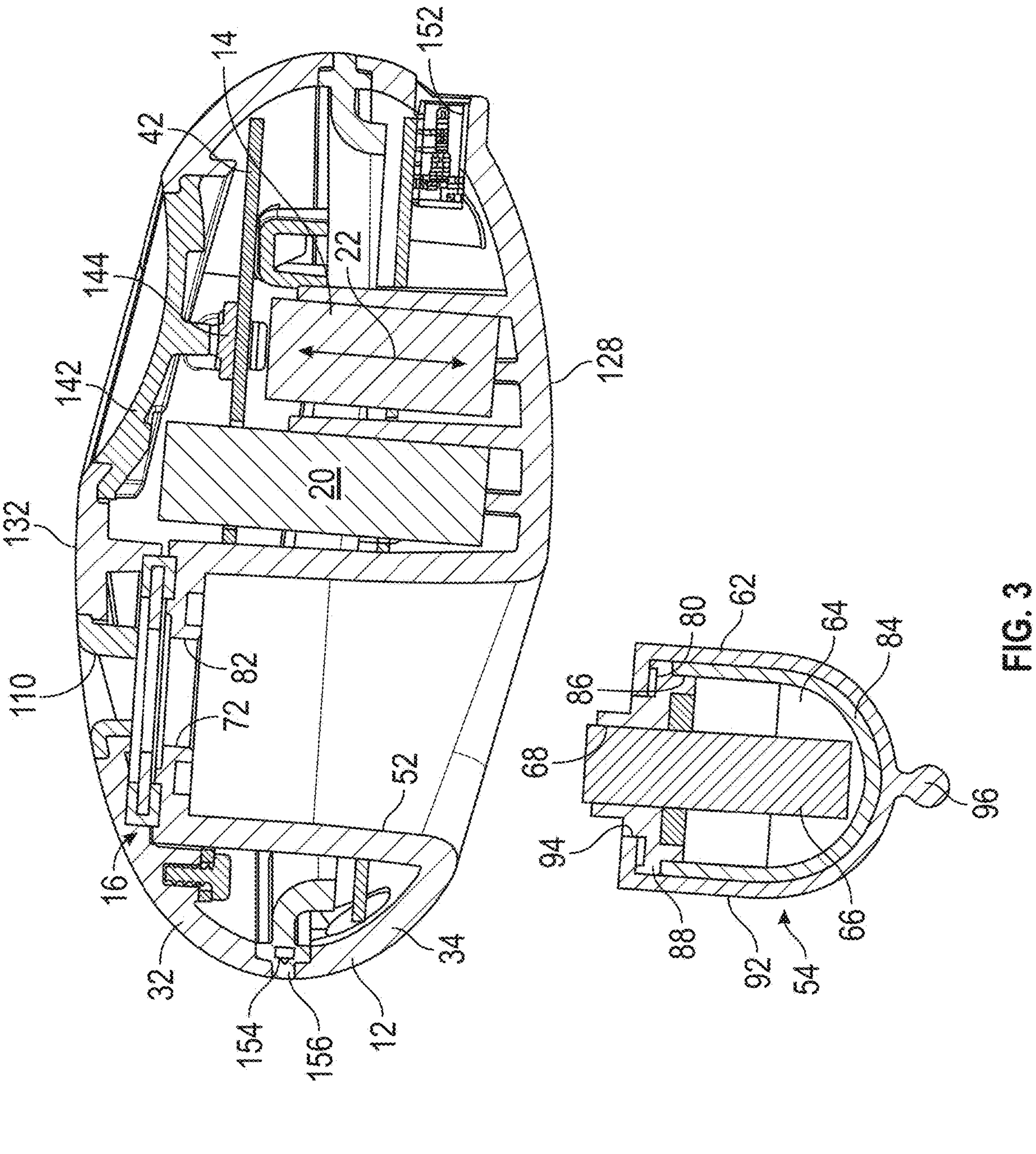
FIG. 3 a cross-sectional view of the relaxation device, showing the arrangement of a vibrator, processing device, and power source within an enclosure.
Figure 4:
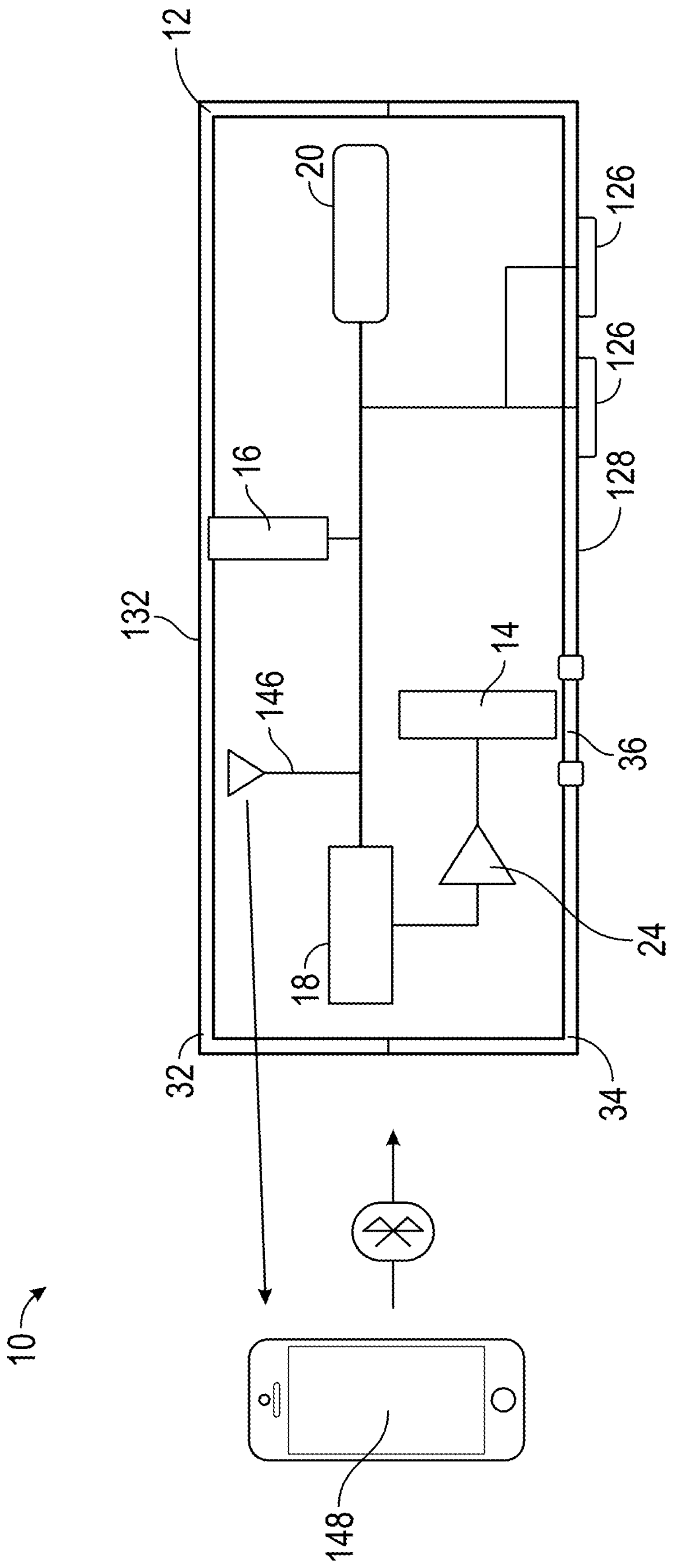
FIG. 4 is a schematic depiction of a relaxation system including the relaxation device.

FIG. 1 depicts a relaxation device 10 that is intended to rest on a person's sternum for guiding a user in paced breathing to encourage relaxation and/or sleep induction. The relaxation device 10 integrates vibration and scent release mechanisms within an enclosure 12. As seen in FIGS. 3 and 4, the relaxation device 10 includes a vibrator 14 in the enclosure 12 and a scent release mechanism 16 at least partially mounted within the enclosure 12. The relaxation device 10 also includes at least one processing device, which can include a processing unit 18 (schematically depicted in FIG. 4) and other components examples of which will be described in more detail below. The at least one processing device controls the operation of both the vibrator 14 and the scent release mechanism 16, allowing for synchronized or independent activation of these features. The relaxation device 10 also includes a power source 20 in the enclosure 12 and electrically connected with the at least one processing device, the vibrator 14 and the scent release mechanism 16.

The vibrator 14 is mounted within the enclosure 12 and is configured to impart a force on at least a portion of the enclosure 12. The vibrator 14 can be designed to produce linear motion substantially along a single axis 22, such as a speaker coil or a linear vibration motor. The vibrator 14 could also be a rotary vibrator, e.g., an eccentric rotating mass (ERM) motor which generates multidirectional vibrations.

In a more particular example, the vibrator 14 can be a linear vibration motor designed to operate within a specific frequency range that can provide effective haptic sensations to the user while remaining relatively quiet to the user. Infrasonic sound, also known as low frequency sound, is a type of sound wave with a frequency below the human hearing range, which is generally 20 Hertz (Hz) or lower. The relaxation device 10 can be configured such that the linear vibration motor operates at frequencies between 45-100 Hz, which is near the infrasonic range. The linear vibration motor can have a resonant frequency between 45-100 Hz. More specifically, the linear vibration motor can have a resonant frequency between 70-90 Hz.

When the vibrator 14 is a linear vibration motor, the linear vibration motor can be designed to provide significant vibration force while maintaining energy efficiency and quiet operation. The linear vibration motor can be configured to generate a root mean square acceleration of at least 0.2 $g^2$/Hz. This measure of vibration intensity ensures that the device provides a noticeable haptic cue to the user while also stimulating the vagus nerve, which runs under the sternum, when the relaxation device 10 is resting on the user's sternum. The linear vibration motor can be configured to achieve the aforementioned acceleration for every 200 mW of power consumed. This high efficiency allows for extended operation times and makes the relaxation device 10 suitable for portable, battery-powered use.

The operation of the vibrator 14 is controlled by the at least one processing device, which can include the processing unit 18 positioned within the enclosure. The at least one processing device can generate a sine wave signal to drive the vibrator 14. The amplitude of the sine wave can be varied over time, allowing for dynamic vibration patterns, e.g., to create pulsing effects or gradually increase or decrease the intensity of the vibration. With reference to FIG. 4, an amplifier 24 may be used to boost the sine wave signal before it reaches the vibrator 14. The amplifier 24 could be an audio amplifier or an operational amplifier, with either fixed or adjustable gain. The use of an amplifier 24 allows the device to achieve higher vibration intensities when desired.

Figure 2:
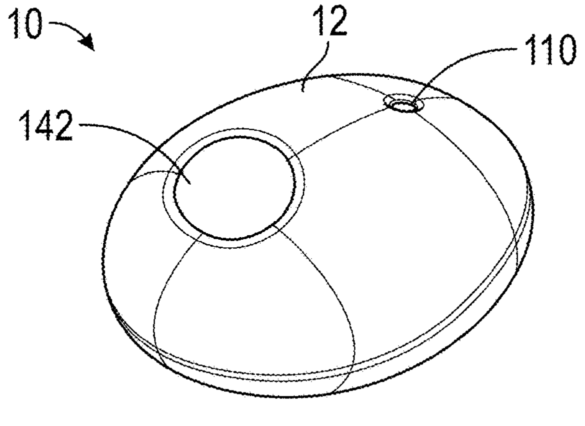
FIG. 2 is a perspective view of an example of the relaxation device of FIG. 1.

The relaxation device 10 includes an enclosure 12 that can take the form shown in FIG. 2; however, the enclosure 12 can take other forms as well. The enclosure 12 is designed to be compact and portable, allowing users to carry and use the relaxation device 10 in various settings. The enclosure 12 may be made of a suitable material such as plastic or metal that can effectively transmit vibrations while also providing durability and protection for the internal components. The enclosure 12 may be designed in various shapes, such as spherical, cylindrical, or ergonomically contoured to fit comfortably on a user's sternum or against different parts of the body. The specific shape chosen can optimize both the transmission of vibrations and user comfort.

With reference to FIGS. 2 and 3, the enclosure 12 can include an upper shell 32 connected to a lower shell 34 via conventional fastening methods including fasteners, adhesives, welding and the like. If desired, and schematically depicted in FIG. 4, the enclosure 12 can include a movable outer wall portion 36 that is directly influenced by the vibrator 14. In some embodiments, the vibrator 14 can be directly connected to the movable outer wall portion 36. This allows the vibration to be directly transferred to the surface that comes into contact with the user. The movable outer wall portion 36 can be connected to a relatively fixed outer wall portion, which in the embodiment illustrated in FIG. 4 is the lower shell 34, via a resilient ring 38. This resilient ring 38 allows for controlled movement of the movable outer wall portion 36 with respect to the relatively fixed outer wall portion, e.g., the lower shell 34, while maintaining the integrity of the enclosure 12 and preventing ingress of dust or moisture into the interior of the enclosure 12. The movable outer wall portion 36 may be made of a slightly more flexible material than the fixed outer wall portion to enhance vibration transmission. The size and shape of the movable outer wall portion 36 can be optimized to provide an effective contact area for the user while maintaining the desired vibration characteristics. When the vibrator 14 imparts a force to the movable outer wall portion 36, the movable outer wall portion 36 moves relative to the fixed outer wall portion. This movement is typically very small (in the range of micrometers to a few millimeters) while being sufficient to create the desired haptic effect.

The at least one processing device, which can include the processing unit 18 in FIG. 4, is in electrical communication with the vibrator 14 and the scent release mechanism 16. The at least one processing device serves as the central control unit for the relaxation device 10. It may comprise one or more microprocessors, microcontrollers, or other suitable integrated circuits, which can be mounted on a circuit board 42 (FIG. 3), capable of executing instructions stored in a memory component. The memory component, which may be integrated with or separate from the processing unit 18 depicted in FIG. 4, can store firmware, software instructions, and data necessary for the operation of the relaxation device 10.

Figure 5:
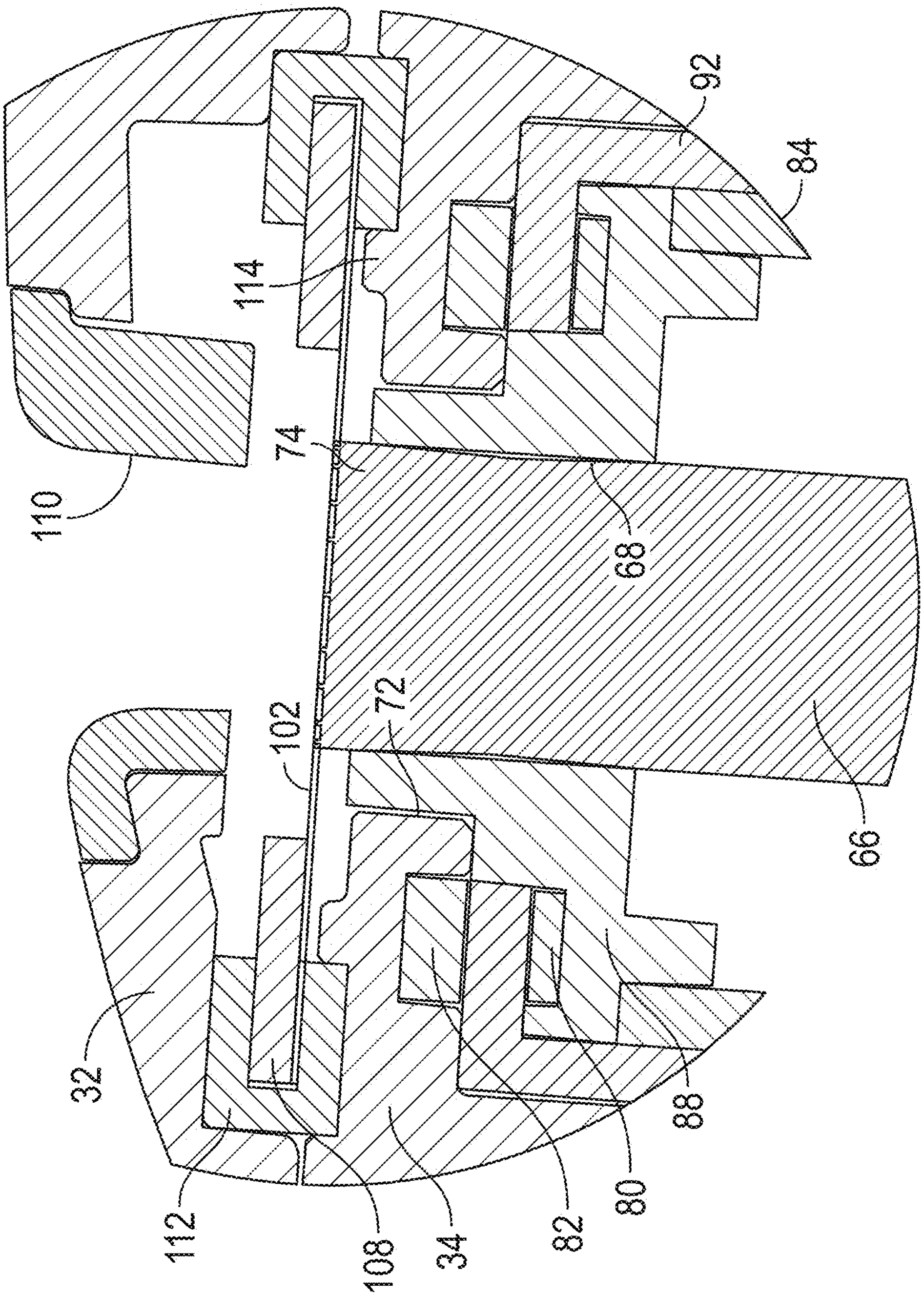
FIG. 5 is a close up cross-sectional view of a replaceable scent capsule received in a scent capsule cavity and cooperating with a scent release mechanism of the relaxation device.

The relaxation device 10 also includes the scent release mechanism 16, which is at least partially mounted within the enclosure 12. As detailed in FIG. 3, the enclosure 12 defines a scent capsule cavity 52 and a replaceable scent capsule 54 is receivable in the scent capsule cavity 52 and operably connectable with the scent release mechanism 16. With reference back to FIG. 3, the replaceable scent capsule 54 includes a capsule housing 62 containing a scent solution 64. A capillary wick 66 extends from an interior of the capsule housing 62 through a wick opening 68 to the exterior of the capsule housing 62. The capsule housing 62 may have a volume between 0.5 and 3.0 mL, and the capillary wick 66 may have a diameter between 3 and 8 mm. FIG. 5 depicts a close up cross-sectional view of the replaceable scent capsule 54 received in the scent capsule cavity 52 and cooperating with the scent release mechanism 16. The enclosure 12 defines a wick-receiving opening 72 (most clearly seen in FIG. 3) within the scent capsule cavity 52. A free end 74 of the capillary wick 66 is received in or through the wick-receiving opening 72 when the replaceable scent capsule 54 is properly received within the scent capsule cavity 52 for cooperation with the scent release mechanism 16, which is shown in FIG. 5. The free end 74 of the capillary wick 66 does not extend a substantial distance, e.g., less than a few millimeters and preferably less than 2.5 mm, from the capsule housing 62.

To secure the replaceable scent capsule 54 within the scent capsule cavity 52, a magnetic connector 80 is mounted to the capsule housing 62. This magnetic connector 80 cooperates with a magnetic element 82 positioned within the scent capsule cavity 52 of the enclosure 12. The free end 74 of the capillary wick 66 is received in or through the wick-receiving opening 72 when the replaceable scent capsule 54 is received within the scent capsule cavity 52 with the magnetic element 82 cooperating with the magnetic connector 80.

In the embodiment of the replaceable scent capsule 54 depicted in FIG. 3, the capsule housing 62 includes an inner capsule wall 84, which is generally dome shaped. The inner capsule wall 84 includes a plug opening 86 at an end that is inserted furthest into the scent capsule cavity 52. A plug 88 is inserted into the plug opening 86. The plug 88 includes the wick opening 68 and with the capillary wick 66 received in the wick opening 68 closes off the plug opening 86. The magnetic connector 80 is trapped between the plug 88 and a sleeve 92 that covers at least a portion of the inner capsule wall 84 and contacts the plug 88 at a radial shoulder 94. In the embodiment of the replaceable scent capsule 54 depicted in FIG. 3, the sleeve 92 can be made from a more resilient material than the inner capsule wall 84. For example, the sleeve 92 can be made from silicone, and the inner capsule wall 84 can be made from a more rigid plastic or glass, for example. A tab 96 can be formed on the sleeve 92 opposite the end through which the capillary wick 66 extends. With the sleeve 92 being made from a relatively resilient material, if the tab 96 were to contact the user's skin while in use, there will be relatively little discomfort. By being made from a relatively resilient material, the sleeve 92 provides a gasket material covering the magnetic connector 80. The sleeve 92 is shown as covering the entirety of the inner capsule wall 84 in FIG. 3, but it may only cover a portion thereof, while still sealing the plug 88 to the inner capsule wall 84. With the magnetic connector 80 being sandwiched between the gasket material of the sleeve 92 and the plug 88, resiliency is provided when the scent capsule 54 is inserted into the scent capsule cavity 52.

The scent release mechanism 16 further includes a disk 102 with a plurality of apertures 104. This disk 102 covers the wick-receiving opening 72 within the scent capsule cavity 52. When the replaceable scent capsule 54 is properly inserted, the free end 74 of the capillary wick 66 is received through the wick-receiving opening 72 and contacts the disk 102, which is shown in FIG. 5. As more clearly seen in FIG. 5, however, the capillary wick 66 does not extend a substantial distance, e.g., less than a few millimeters and preferably less than one millimeter, from the plug 88. Such a construction discourages users from contacting and/or grabbing the capillary wick 66. A piezoelectric atomizer 108 is connected to the disk 102. When energized, the piezoelectric atomizer 108 vibrates the disk 102, drawing the scent solution from the capillary wick 66 and atomizing it as it passes through the apertures 104 in the disk 102. The atomized scent solution then exits the relaxation device 10 through a scent outlet 110 provided in the enclosure 12.

The scent release mechanism 16 depends on capillary action to draw the scent solution 64 from the replaceable scent capsule 54 through the capillary wick 66 to the disk 102. As such, the scent solution 64 is formulated to have a viscosity and specific gravity that is nearer to that of distilled water at 20 degrees C. as compared to many oils (e.g., canola oil has a viscosity of around 46 centipoise at 20 degrees C.). As such, the scent solution 64 can be formulated to have a viscosity below 10 centipoise at 20 degrees C. In addition or alternatively, the scent solution 64 can be formulated to have a specific gravity within 20% of distilled water at 20 degrees C. Such a formulation can inhibit clogging and enable effective dispersion.

Figure 6:
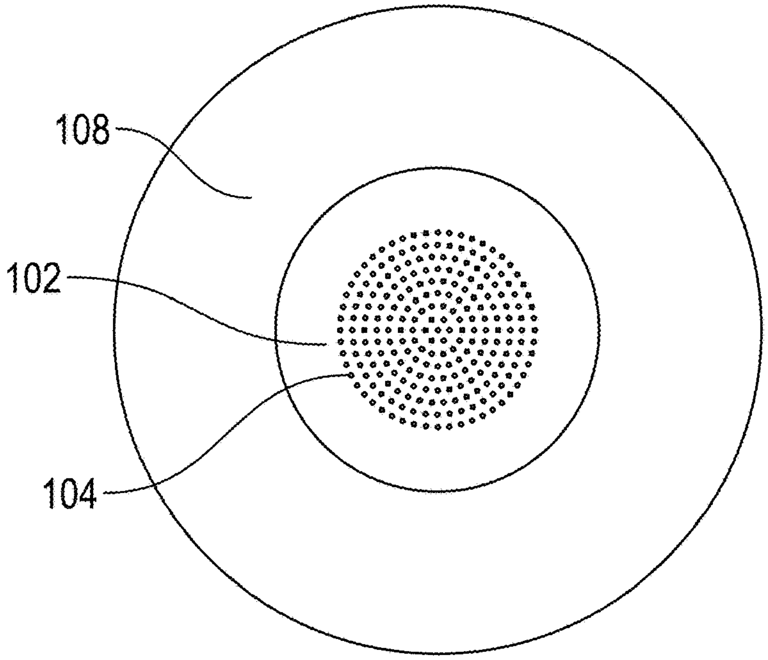
FIG. 6 top view of a disk and atomizer for the scent release mechanism.

The disk 102 can be made from a durable, non-reactive material that can withstand repeated vibrations and exposure to various scent solutions. Suitable materials may include certain metals (such as stainless steel or titanium) or high-performance polymers that offer chemical resistance and maintain their properties over time. In one embodiment and with reference to FIG. 6, the disk 102 includes at least 50 apertures 104, providing a sufficient number of pathways for the scent solution to be effectively atomized. Each aperture 104 can a maximum diameter between 1 μm and 15 μm. This specific size range is chosen to generate the optimal droplet size for the atomized scent solution, ensuring that it can be easily dispersed into the air and effectively perceived by the user. The apertures 104 can be distributed across the surface of the disk 102 in a pattern designed to promote even and efficient atomization. This distribution may be uniform or may follow a specific pattern optimized for particular design and atomization requirements. The disk 102 is positioned so that it contacts the free end 74 of the capillary wick 66 when the replaceable scent capsule 54 is properly inserted into the scent capsule cavity 52. This direct contact ensures efficient transfer of the scent solution from the capillary wick 66 for atomization through the apertures 104. The disk 102 is connected to the piezoelectric atomizer 108 in a manner that allows for efficient transfer of vibrational energy as high-frequency vibrations of the disk 102 cause the scent solution to break into fine droplets as it passes through the apertures 104 in route to a scent outlet 110.

The piezoelectric atomizer 108 is designed to operate at a high frequency, typically in the ultrasonic range (>20 kHz). More particularly, the piezoelectric atomizer 108 can operate at frequencies between 50-250 kHz, and most preferably at a resonant frequency of about 113 kHz. This high-frequency provides effective atomization and helps ensure that the relaxation device 10 operates very quietly. A different type of mister is known that uses a piezoelectric atomizer with resonant frequencies around 2 MHz, but these are meant to be immersed in the liquid being dispersed and can consume quite a lot of power not making them suitable for use with such a small device. The piezoelectric atomizer 108 is powered by a driver circuit to provide the necessary high-frequency alternating current. This driver circuit is controlled by the at least one processing device and/or the processing unit 18 depicted in FIG. 4 to manage the atomization process.

The piezoelectric atomizer 108 is mounted within the enclosure 12 using a piezoelectric mount 112 made from a dampening material. With reference to FIG. 5, the lower shell 34 can include a locating ridge 114. The piezoelectric mount 112 is sandwiched between the upper shell 32 and the lower shell 34 of the enclosure 12 in the illustrated embodiment. This mounting arrangement isolates the vibrations of the piezoelectric atomizer 108 from the rest of the relaxation device 10 preventing unwanted noise or interference with other components. The piezoelectric mount 112 being made from a dampening material acts as a gasket, inhibiting the ingress of scent solution into the electronic interior compartment of the enclosure 12 where the vibrator 14, the processing unit 18, and the power source 20 are located. By providing the gasket material, e.g., the sleeve 92 in FIGS. 3 and 5, at the interface of the scent capsule 54 and the enclosure 12, or lower shell 34, the scent capsule 54 may be able to move, even only slightly, as the disk 102 contacts the capillary wick 66 and the cooperation between magnetic connector 80 and magnetic element 82 can still retain the scent capsule 54 in the scent capsule cavity 52.

The relaxation device 10 can also be designed to detect the user's cardiac signals, enabling the relaxation device 10 to adapt its operation based on the user's physiological response. As schematically depicted in FIG. 4, the processing unit 18, which can make up part of at least one processing device, can interface with electrodes 126, which can be dry ECG (electrocardiogram) biopotential electrodes that do not require the typical electrolytic conductive gel and skin preparation as compared to wet electrodes. At least two, and perhaps more, electrodes 126 can be mounted to the enclosure 12 and in electrical communication with the processing unit 18. The electrodes 126 are mounted to the enclosure 12 in a manner such that when the enclosure 12 is placed on the user's sternum (see FIG. 1) ionic currents from the user's body surface are converted into electrical signals for later processing by the at least one processing device, which can be useful to adaptively adjust the vibration patterns.

The enclosure 12 includes a lower surface 128, which is depicted in FIGS. 3 and 4, configured to contact a user's skin and an upper surface 132 opposite and spaced away from the lower surface 128. The electrodes 126 have contact surfaces that are flush with or extend outwardly from an outer surface, and in the illustrated embodiment the lower surface 128, of the enclosure 12. The electrodes 126 are in electrical communication with the processing unit 18 and can be used to measure the user's cardiac signals. The upper surface 132 defines the scent outlet 110 (see FIG. 3) through which atomized scent solution passes.

The at least one processing device, which includes the processing unit 18, is programmed to perform several functions of the relaxation device 10.

The at least one processing device controls the operation of the vibrator 14, which can include adjusting the frequency, intensity, and pattern of vibrations based on predefined settings or user input. The at least one processing device may implement various vibration profiles designed to induce different relaxation states. The at least one processing device manages the operation of the scent release mechanism 16 such as controlling the timing and duration of scent release, as well as potentially adjusting the intensity of scent release by modulating the operation of the piezoelectric atomizer 108.

When the relaxation device 10 is equipped with electrodes 126, the at least one processing device can process and analyze the cardiac signals detected by the electrodes 126. This analysis may involve calculating various cardiac metrics such as heart rate, heart rate variability, or other relevant parameters. Based on the analysis of cardiac signals, the at least one processing device can adapt the operation of the vibrator 14 and scent release mechanism 16. For example, if the detected cardiac signals indicate a high stress level, the at least one processing device might intensify the vibration and scent release to promote relaxation.

The relaxation device 10 includes an on/off button 142 operably connected with an on/off switch 144 that is in electrical communication with the at least one processing device. The on/off switch 144 can be mounted to the circuit board 42 located within the enclosure 12. The on/off button 142 can be offset from the scent outlet 110 along the upper surface 132 of the enclosure 12. Where the relaxation device 10 includes user interface elements such as buttons, touch sensors, or displays, the at least one processing device manages these interfaces, interpreting user inputs and providing appropriate feedback or device responses.

With reference to FIG. 4, wireless communication modules 146 (e.g., Bluetooth Low Energy) can be provided as part of the at least one processing device to provide communication between a smart phone 148. In such an instance, the processor on the smart phone 148 can form a component of the at least one processing device and the smart phone 148 and any connected application running on the smart phone 148 in combination with the relaxation device 10 can make up a relaxation system.

With reference to FIG. 3, a charging port 152 is provided in the enclosure 12 for charging the relaxation device 10. The charging port 152 is in electrical communication with the processing unit 18 and the power source 20, which can be a rechargeable battery. The at least one processing device can also be provided to control LEDs 154 (only one depicted in FIG. 3) that can be mounted in a light ring 156 positioned between the upper shell 32 and the lower shell 34.

Figure 7:
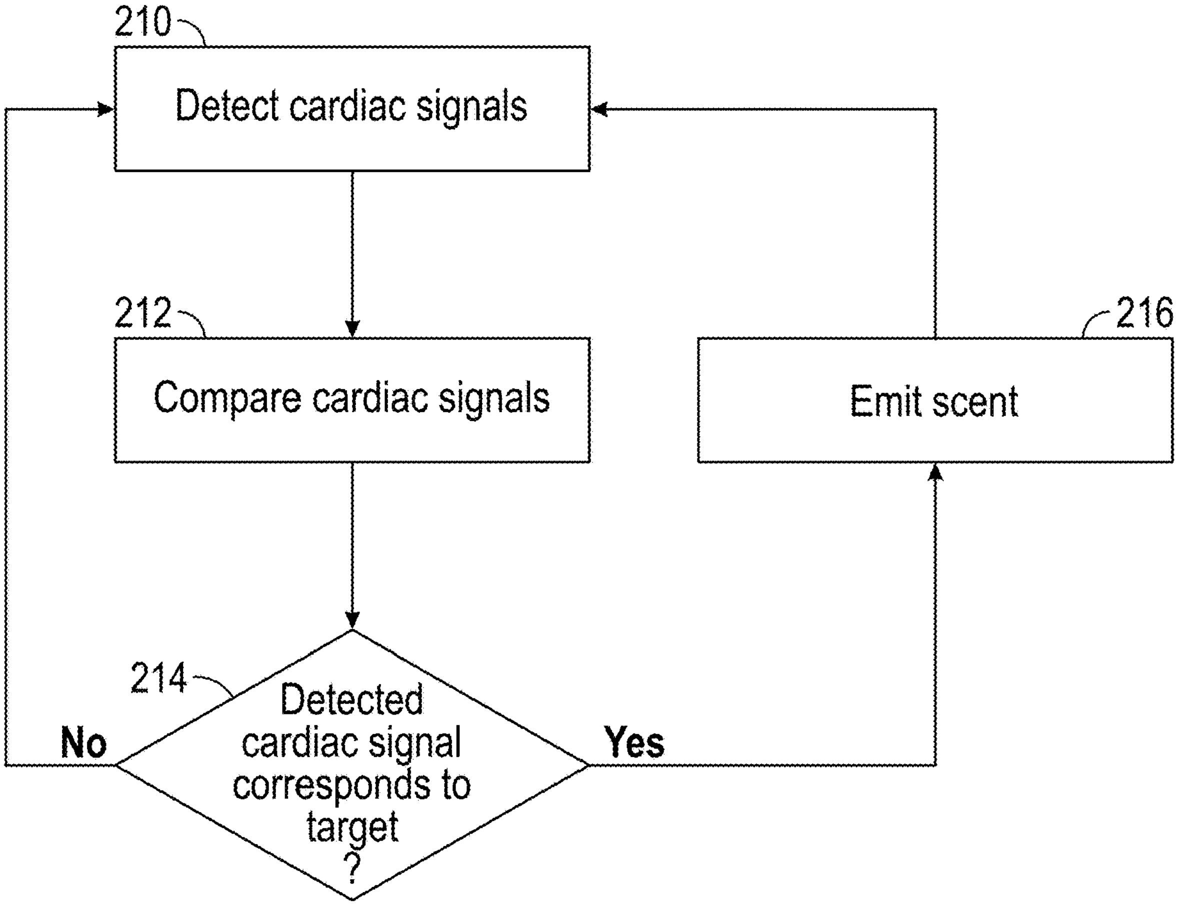
FIG. 7 is a flow diagram depicting an example of a method of operating the relaxation system.

A method of operating the relaxation device 10 will be described with reference to FIG. 7. The process shown in FIG. 7 occurs while controlling the vibrator 14 disposed in the enclosure 12 to induce vibrations of the enclosure 12. The vibrator 14 can be controlled to match the inhalation phase and exhalation phase of a desired breathing pattern where the vibrator 14 is turned on during the inhalation phase and exhalation phase of the desired breathing pattern.

The process in FIG. 7 will be described with reference to measuring the user's cardiac signals to determine if the detected cardiac signal corresponds to a target signal, and the process could be employed with measuring cardiac signals such as heart rate (HR), heart rate variability (HRV), respiratory sinus arrhythmia (RSA), power and frequency. This correspondence does not need to be an exact match between the detected cardiac signal and the target cardiac signal; instead, the correspondence could be within an acceptable range. At 210, a person's cardiac signals are detected via the electrodes 126 mounted to the enclosure 12 and the at least one processing device, which can include the processing unit 18 and/or the processor found in the smart phone 148. Typically, the enclosure 12 is placed on the user's sternum, as shown in FIG. 1, while the user is lying down on her back. As mentioned above, other cardiac metrics such as HR, RSA, power or frequency could also be detected at 210.

At 212, the detected cardiac signals are compared to a target cardiac signal via the at least one processing device, which can include software running on the processing unit 18 and/or the processor found in the smart phone 148. The target cardiac signal can be the person's greatest HRV, which is associated with the person's resonance frequency and is associated with the person's optimal state for relaxation and sleep. If desired, other detected cardiac metrics can be compared to the appropriate target cardiac measurement at 212.

At 214, if the detected cardiac signals correspond to the target cardiac signal, then the process moves to 216 and a scent solution is emitted from the enclosure 12 via a scent release mechanism 16. Emitting the scent solution from the enclosure 12 via the scent release mechanism 16 can include atomizing scent solution 64 drawn from a capillary wick 66 disposed in the replaceable scent capsule 54 received in the enclosure 12. If, at 214, the detected cardiac signals do not correspond to the target cardiac signal, then the process can return to 210 and detect the person's cardiac signals via the electrodes 126 mounted to the enclosure 12. In other words, no scent may be emitted, which can indicate to the user that the target cardiac signal has not been achieved.

It will be appreciated that various of the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A relaxation device comprising:
- an enclosure dimensioned to rest on a person's sternum for guiding a user in paced breathing;
- a vibrator in the enclosure and configured to induce vibrations of at least a portion of the enclosure rested on the person's sternum in use;
- a scent release mechanism at least partially mounted within the enclosure;
- at least one processing device in electrical communication with the vibrator and the scent release mechanism, the at least one processing device being configured for synchronized activation of the vibrator and the scent release mechanism; and
- a power source in the enclosure and electrically connected with the at least one processing device, the vibrator and the scent release mechanism.

2. The relaxation device of claim 1, wherein the enclosure defines a scent capsule cavity and the relaxation device further comprising a replaceable scent capsule receivable in the scent capsule cavity and operably connectable with the scent release mechanism.

3. The relaxation device of claim 2, wherein the replaceable scent capsule includes a capsule housing, a scent solution in the capsule housing, and a capillary wick extending from an interior of the capsule housing through a wick opening in the capsule housing to an exterior of the capsule housing.

4. The relaxation device of claim 3, wherein the scent solution has a viscosity below 10 centipoise at 20 degrees C.

5. The relaxation device of claim 3, wherein the scent solution has a specific gravity within 20% of distilled water at 20 degrees C.

6. The relaxation device of claim 3, wherein the replaceable scent capsule includes a magnetic connector mounted to the capsule housing and the relaxation device further includes a magnetic element positioned within the scent capsule cavity, the magnetic element cooperates with the magnetic connector to retain the replaceable scent capsule within the scent capsule cavity.

7. The relaxation device of claim 6, wherein the enclosure defines a wick-receiving opening within the scent capsule cavity, a free end of the capillary wick being received through the wick-receiving opening when the replaceable scent capsule is received within the scent capsule cavity with the magnetic element cooperating with the magnetic connector.

8. The relaxation device of claim 7, wherein the scent release mechanism includes a disk including a plurality of apertures and the wick-receiving opening is covered by the disk.

9. The relaxation device of claim 8, wherein the scent release mechanism includes a piezoelectric atomizer connected with the disk, the piezoelectric atomizer configured to be energized to vibrate the disk to draw the scent solution from the capillary wick and to atomize the scent solution as the scent solution passes through the plurality of apertures on route to a scent outlet provided in the enclosure.

10. The relaxation device of claim 9, wherein the piezoelectric atomizer is configured to operate at a frequency less than 250 KHz.

11. The relaxation device of claim 10, wherein the frequency at which the piezoelectric atomizer is configured to operate is greater than 50 kHz.

12. The relaxation device of claim 1, further comprising electrodes mounted to the enclosure, each electrode including a contact surface flush with or extending outwardly from an outer surface of the enclosure and being in electrical communication with the at least one processing device.

13. The relaxation device of claim 12, wherein the at least one processing device is configured:

to measure at least one cardiac metric based on signals received from the electrodes and provide a detected cardiac metric; and to control operation of the scent release mechanism based on the detected cardiac metric.

14. The relaxation device of claim 1, wherein the enclosure includes a lower surface configured to contact the user's skin and an upper surface opposite and spaced away from the lower surface, wherein the upper surface defines a scent outlet through which an atomized scent solution passes and the relaxation device further including an on/off button operably connected with an on/off switch that is in electrical communication with the at least one processing device, the on/off button being offset from the scent outlet along the upper surface of the enclosure.

15. A relaxation device, comprising:

an enclosure dimensioned to rest on a person's sternum for guiding a user in paced breathing, wherein the enclosure defines a scent capsule cavity and a wick-receiving opening within the scent capsule cavity;

a vibrator in the enclosure and configured to induce vibrations of at least a portion of the enclosure;

a scent release mechanism at least partially mounted within the enclosure, wherein the scent release mechanism includes a disk including a plurality of apertures and the wick-receiving opening is covered by the disk, wherein the scent release mechanism further includes a piezoelectric atomizer connected with the disk;

at least one processing device in electrical communication with the vibrator and the scent release mechanism, the at least one processing device being configured to control operation of the vibrator and the scent release mechanism; and a power source in the enclosure and electrically connected with the at least one processing device, the vibrator and the scent release mechanism;

a magnetic element positioned within the scent capsule cavity; and a replaceable scent capsule receivable in the scent capsule cavity and operably connectable with the scent release mechanism, wherein the replaceable scent capsule includes a capsule housing, a scent solution in the capsule housing, a capillary wick extending from an interior of the capsule housing through a wick opening in the capsule housing to an exterior of the capsule housing, and a magnetic connector mounted to the capsule housing, the magnetic element cooperates with the magnetic connector to retain the replaceable scent capsule within the scent capsule cavity, wherein a free end of the capillary wick is received through the wick-receiving opening when the replaceable scent capsule is received within the scent capsule cavity with the magnetic element cooperating with the magnetic connector, wherein the disk contacts the free end of the capillary wick when the replaceable scent capsule is received within the capsule housing with the magnetic element cooperating with the magnetic connector, wherein the piezoelectric atomizer is configured to be energized to vibrate the disk to draw the scent solution from the capillary wick to atomize the scent solution as the scent solution passes through the plurality of apertures on route to a scent outlet provided in the enclosure; and wherein the capsule housing includes an inner capsule wall, a plug opening at an end of the capsule housing that is inserted furthest into the scent capsule cavity, a plug, which includes the wick opening, inserted into the plug opening and a sleeve that covers at least a portion of the inner capsule wall and contacts the plug, wherein the sleeve is made from a more resilient material than the inner capsule wall and the magnetic connector is trapped between the plug and the sleeve.

16. The relaxation device of claim 15, wherein the disk includes at least 50 apertures and each aperture has a maximum diameter between 1 μm and 15 μm.

17. The relaxation device of claim 15, wherein the scent release mechanism includes a piezoelectric mount and the enclosure includes an upper shell connected with a lower shell, wherein the piezoelectric mount is made from a dampening material and is sandwiched between the upper shell and the lower shell.

18. The relaxation device of claim 17, wherein the piezoelectric mount operates as a gasket inhibiting ingress of the scent solution into an electronic interior compartment of the enclosure in which the vibrator, the at least one processing device and the power source are located.

19. A relaxation device comprising:

an enclosure dimensioned to rest on a person's sternum for guiding a user in paced breathing, wherein the enclosure defines a scent capsule cavity and a scent outlet;

a vibrator in the enclosure and configured to induce vibrations of at least a portion of the enclosure rested on the person's sternum in use;

a scent release mechanism at least partially mounted within the enclosure;

at least one processing device in electrical communication with the vibrator and the scent release mechanism, the at least one processing device being configured to control operation of the vibrator and the scent release mechanism; and a power source within the enclosure and positioned between the scent capsule cavity and the vibrator along a cross section taken along a longest dimension of the enclosure, the power source being electrically connected with the at least one processing device, the vibrator and the scent release mechanism.

20. The relaxation device of claim 19, wherein the processing device is further configured for synchronized activation of the vibrator and the scent release mechanism.

* * * * *